US011398294B2

United States Patent
Song et al.

(10) Patent No.: US 11,398,294 B2
(45) Date of Patent: Jul. 26, 2022

(54) METHOD FOR CONTROLLING THE QUALITY OF TRADITIONAL CHINESE PATENT MEDICINES BASED ON METAGENOMICS

(71) Applicant: Institute of Medicinal Plant Development, Chinese Academy of Medical Science, Beijing (CN)

(72) Inventors: Jingyuan Song, Beijing (CN); Tianyi Xin, Beijing (CN); Zhichao Xu, Beijing (CN); Jing Jia, Beijing (CN)

(73) Assignee: Institute of Medicinal Plant Development, Chinese Academy of Medical Science, Beijing (CN)

( * ) Notice: Subject to any disclaimer, the term of this patent is extended or adjusted under 35 U.S.C. 154(b) by 155 days.

(21) Appl. No.: 16/085,988

(22) PCT Filed: Jun. 28, 2017

(86) PCT No.: PCT/CN2017/090449
§ 371 (c)(1),
(2) Date: Sep. 17, 2018

(87) PCT Pub. No.: WO2019/000254
PCT Pub. Date: Jan. 3, 2019

(65) Prior Publication Data
US 2020/0126633 A1 Apr. 23, 2020

(51) Int. Cl.
*G16H 70/40* (2018.01)
*G16B 30/20* (2019.01)
(Continued)

(52) U.S. Cl.
CPC ........... *G16B 20/50* (2019.02); *C12Q 1/6869* (2013.01); *C12Q 1/6895* (2013.01); *G16B 30/20* (2019.02);
(Continued)

(58) Field of Classification Search
CPC ...... G16H 20/90; G16H 70/40; C12Q 1/6895; C12Q 1/6869; G16B 30/20; G16B 35/20; G16B 99/00; G16B 35/00; G16B 30/00
See application file for complete search history.

(56) References Cited

U.S. PATENT DOCUMENTS

2015/0113679 A1* 4/2015 Mackenzie .............. A01H 3/00
800/265
2015/0284796 A1* 10/2015 Marden .................. G16B 30/20
506/2

(Continued)

FOREIGN PATENT DOCUMENTS

| CN | 105861486 A | 8/2016 |
|---|---|---|
| CN | 106754872 A | 5/2017 |

OTHER PUBLICATIONS

Cheng, Xinwei, et al. "Biological ingredient analysis of traditional Chinese medicine preparation based on high-throughput sequencing: the story for Liuwei Dihuang Wan." Scientific reports 4.1 (2014): 1-12. (Year: 2014).*

(Continued)

*Primary Examiner* — Jesse P Frumkin
(74) *Attorney, Agent, or Firm* — Knobbe Martens Olson & Bear, LLP

(57) ABSTRACT

A method for controlling the quality of traditional Chinese patent medicines is based on metagenomics. The method includes extracting genomic DNA of a sample of the traditional Chinese patent medicine, constructing a library of the genomic DNA based on a high-throughput sequencing platform, and performing metagenomic sequencing. The data obtained from the metagenomic sequencing is processed to obtain the ITS2 sequence of the traditional Chinese patent medicine sample A BLAST alignment is performed on the ITS2 sequence in the DNA Barcoding System for Identifying Herbal Medicine, to obtain species identification results.

(Continued)

The obtained identification results are compared with the labeled species of the traditional Chinese patent medicine to obtain a conclusion about the quality of the traditional Chinese patent medicine sample.

10 Claims, 7 Drawing Sheets

(51) Int. Cl.
- *G16B 35/20* (2019.01)
- *C12Q 1/6869* (2018.01)
- *C12Q 1/6895* (2018.01)
- *G16H 20/90* (2018.01)
- *G16B 20/50* (2019.01)

(52) U.S. Cl.
CPC ............ *G16B 35/20* (2019.02); *G16H 20/90* (2018.01); *G16H 70/40* (2018.01)

(56) References Cited

U.S. PATENT DOCUMENTS

2017/0335410 A1* 11/2017 Driscoll ............... C12Q 1/6888
2019/0032153 A1* 1/2019 Lu ......................... C12Q 1/6855

OTHER PUBLICATIONS

Han, Jianping, et al. "An authenticity survey of herbal medicines from markets in China using DNA barcoding." Scientific reports 6.1 (2016): 1-9. (Year: 2016).*

International Search Report received in PCT Application No. PCT/CN2017/090449, dated Apr. 4, 2018.

Xiao-chen, Chen et al., "Study on Metagenomics and Genuine Traditional Chinese Medicinal Materials," Chinese Traditional and Herbal Drugs, Dec. 31, 2012.

* cited by examiner

Figure 1

```
>NODE_42_length_268_cov_84.763654
TAGGCCGGAGGGGCACGTCTGCCTGGGCGTCAAGCATGCGTCACCCCCGACTCCGTCGTCTCGGAGCGCGGTGGTGATATTGGCCCCGGTGCGTCG
CGCGGTCGGCCAAAACGAGCCCTTGACGGCCAGTGTCACGATCAGTGGTGGTTGACGTGCCTCTTTCCGGAGATGGATGTCGTGCCGCGTGCGTGTC
AATGGGCCACGGCGGACCTTTCGGTGCTCACGGAGCACTGTCCTGCGACCCAGGTCAGGCGGGCCACCCGCGTCAGGTCAGTTTAAGCATATCAATAAGCG
```

| | |
|---|---|
| Search Result | |
| Nearest match: | Akebia trifoliata var. australis [Eflora>Akebia trifoliata subsp. Australis;Akebia trifoliata var. australis[P];Akebia trifoliata subsp. australis] (Akebiae Caulis) |

| Descriptions | | | | |
|---|---|---|---|---|
| Accession | Species | Similarity | Score | E-value |
| 071 | Akebia trifoliata var. australis | 100.0 | 428.0 | e-120 |
| CQ0215 | Akebia trifoliata | 99.1 | 412.0 | e-115 |
| AY029788 | Akebia trifoliata subsp. australis | 98.6 | 412.0 | e-115 |
| JF421460 | Akebia trifoliata subsp. trifoliata | 98.6 | 408.0 | e-114 |
| JF421461 | Akebia trifoliata subsp. australis | 98.6 | 408.0 | e-114 |

>NODE_189_length_251_cov_22.569721
GCGGGTAGTCCCGCCTGACCTGGGGTCACATTCGAAGTGCACAAGTGTGTGCCGCCTAAGGTCCTTGAGCTCACTAAGATGACGCGGATTCGGCGAC
AAGACATGAGGTATTTTACAACCACCAATGTCACGACGTCCGTCGCGAGACTCACTTTTGCGCCAACGCACAACAAGGCACGGCGAGGCCAATTTCCG
CCCCCATACCAGTACAGTCCACGAGGGAGTGAGTGGTTGTGGGCAAAGATGATGGGTGACACCCAGGCAGAGCGTGCCCTC

Search Result

Nearest match: Angelica sinensis [Angelica sinensis(P):Angelica sinensis (Oliv.) Diels] (Angelicae sinensis Radix)

Descriptions

| Accession | Species | Similarity | Score | E-value |
|---|---|---|---|---|
| S0557 | Angelica sinensis | 100.0 | 460.0 | e-129 |
| DG08 | Angelica sinensis | 100.0 | 460.0 | e-129 |
| DG04 | Angelica sinensis | 100.0 | 460.0 | e-129 |
| DG03 | Angelica sinensis | 100.0 | 460.0 | e-129 |
| FJ572042 | Angelica sinensis | 100.0 | 456.0 | e-128 |

Figure 2

```
>NODE_61_length_211_cov_120.587111
GTAATCCGCGCTGACCTGGACTGGGGTCGAGGCTCGGGGAGCTTCCGGGTCAGGGACCGGGGCTGGGGTTCACGGGACCGGGGCTGGGGTTGCCGGCACGACGACGACTCGAGTT
GAGGGACTCAACGACCACCACCAGTCGTGACGCCCCTCGCCGAGGAACTCTCATTTGGCGCGCTCGCCGGGGCACGGAGGCCAGTCTCGCCGCCGCCGCC
CCGCGGGAGGGGGGGTGGCGACGCGATGCGTGACGCCCAGGCAGAC
```

Search Result

Nearest match: Gardenia jasminoides (Gardenia jasminoides[P];Gardenia angusta;) (Gardeniae Fructus)

Description

| Accession | Species | Similarity | Score | E-value |
|---|---|---|---|---|
| RC-CQ0131 | Gardenia jasminoides | 100.0 | 398.0 | e-111 |
| KC533838 | Gardenia jasminoides | 100.0 | 398.0 | e-111 |
| H8Z05 | Gardenia jasminoides | 100.0 | 398.0 | e-111 |
| HAP00254 | Gardenia jasminoides | 100.0 | 398.0 | e-111 |
| GQ434647 | Gardenia jasminoides | 100.0 | 398.0 | e-111 |

Figure 3

>NODE_158_length_297_cov_285.828278
CTTATTGATATGCTTAAACTCAGCGGGTAGCCCGGCTGACCTGAGGTCTCATCACGAGCGGTTCAAAGAGCCTATTGGTTACAGAGCCCAAACTCAGTGGA
GTCACACATGATTGGTCTCGACGTCACTCAACCACCATCATGCCAAACCCTACCATGGACTCAGTTTTGAGCCAACCGTGAGGCCGCAATGCTCACG
GGAAGCCACATTCACCCTGCACAACGAAGTACGTATCGGAGGCAATTGGCATCCGGGTAACGGTCTGTGACACCAGGCAGGGAGAGTGCCGTTGGCCTAAT
GGCTTCGGGCGCAACTTGCGTT Nearest match: Glycyrrhiza uralensis (Glycyrrhiza uralensisFPH (Glycyrrhizae Radix et Rhizoma))

| Accession | Species | Similarity | Score | E-value |
|---|---|---|---|---|
| ZY019 | Glycyrrhiza uralensis | 100.0 | 442.0 | e-124 |
| YC0130MT34 | Glycyrrhiza uralensis | 100.0 | 442.0 | e-124 |
| YC0130MT06 | Glycyrrhiza uralensis | 100.0 | 442.0 | e-124 |
| ZY020 | Glycyrrhiza uralensis | 99.6 | 434.0 | e-121 |
| ZY018 | Glycyrrhiza uralensis | 99.6 | 434.0 | e-121 |

Figure 4

>NODE_290_length_152_cov_17.157894
GGGGGGGGGAGATTGGGCCCCGTGTGCGCCCGGCGCGCGCCGCCAAATGGATCCCGGGCGACGCCACGCCCGGACAAGTGGTGGTTGTTTCCT
CAACTGGTGCTGTGTGCCAAGGGTGCGTCGTTCGGGAGAGAATGAAGATGAGACCAACGGCCATGTGCATCGA

Search Result

Nearest match: Scutellaria baicalensis [Scutellaria baicalensis(P);Scutellaria baicalensis Georgi] (Scutellariae Radix)

Descriptions

| Accession | Species | Similarity | Score | E-value |
|---|---|---|---|---|
| HAP00352 | Scutellaria baicalensis | 100.0 | 361.0 | e-100 |
| FJ883534 | Scutellaria baicalensis | 100.0 | 361.0 | e-100 |
| FJ609732 | Scutellaria baicalensis | 100.0 | 361.0 | e-100 |
| AB557593 | Scutellaria baicalensis | 100.0 | 361.0 | e-100 |

```
>NODE_103_length_236_cov_237.901531
GTAGTCCGCCTGACCTGGGGTCGGGGTCGGAGGCGCAACGGTCGAGGACGGCAACGGGCAAGAGGGTCATGAGAGCTTTTGCTGGGGACGGGTCACCGCACGACAT
GAGAAGAGGCGTTTTACAACACCACCACTGTCGTGACCTCGCAAGACTCGCATTGGGCCAACCGCGCGGGTGAGACACGGGAGGCATTATCCG
CCCTCCGCCTCAACTCCCGCAAGGGAGGAGTGATGGGTTGGGGGCGACGCGGATGCGTGACGCCCAAGGC
```

Search Result

Nearest match: Panax ginseng [Panax ginseng|P] (*Panax ginseng*)

Descriptions

| Accession | Species | Similarity | Score | E-value |
|---|---|---|---|---|
| U41682 | Panax ginseng | 100.0 | 470.0 | e-132 |
| U41680 | Panax ginseng | 100.0 | 470.0 | e-132 |
| AY233326 | Panax ginseng | 100.0 | 466.0 | e-131 |
| HM446504 | Panax ginseng | 100.0 | 464.0 | e-130 |
| HM446503 | Panax ginseng | 100.0 | 464.0 | e-130 |

Figure 7

```
>NODE_134_length_226_cov_58.066372
TCCGCCTGACCTGGGTGCGCGGTGAAGCATCGTCGCAAGACGACACGTTGGGGTCTTTGAAGAGCGTTCCTTCCGTCCGC
ACGGTCGATACGAAGCCCTTGACAACCACCACTAGCGTCGCCTCCGTCCAACGGACTCCTATTTAGGCCAACCCCCGTCG
GCACGGGAGACCAGTCTCGGCCCTGATGGAACGATCCCATGAAGCGGGGGATCGGTCGGCGGAGGCGGTGAGGC
CAGGCA
```

Search Result

| Nearest match: | Saussurea costus [Aucklandia lappa(P)] . Aucklandia lappa [Aucklandia lappa(P)Saussurea costus:] (Aucklandiae Radix) |
|---|---|

Descriptions

| Accession | Species | Similarity | Score | E-value |
|---|---|---|---|---|
| EU257421 | Saussurea costus | 100.0 | 442.0 | e-124 |
| EU257420 | Saussurea costus | 100.0 | 442.0 | e-124 |
| EU257419 | Saussurea costus | 100.0 | 442.0 | e-124 |
| EU239685 | Saussurea costus | 100.0 | 442.0 | e-124 |
| AY914821 | Saussurea costus | 100.0 | 442.0 | e-124 |
| YMX03 | Aucklandia lappa | 100.0 | 442.0 | e-124 |
| YC0139MT21 | Aucklandia lappa | 100.0 | 442.0 | e-124 |
| YC0139MT18 | Aucklandia lappa | 100.0 | 442.0 | e-124 |

METHOD FOR CONTROLLING THE QUALITY OF TRADITIONAL CHINESE PATENT MEDICINES BASED ON METAGENOMICS

TECHNICAL FIELD

The present invention belongs to the technical field of quality control of traditional Chinese patent medicines, herbal products, dietary supplements and the like, and particularly relates to a method for monitoring the quality of traditional Chinese patent medicines based on metagenomic sequencing technology and DNA barcode molecular identification technology.

CROSS-REFERENCED TO RELATED APPLICATIONS

This application is the U.S. National Phase under 35 U.S.C. § 371 of International Application No. PCT/CN2017/090449, filed Jun. 28, 2017, designating the United States of America.

BACKGROUND ART

According to the "*Pharmacopoeia of the People's Republic of China*" (current edition), the methods for the quality control of traditional Chinese patent medicines mainly include microscopic identification, thin layer chromatography (TLC) identification, content determination, fingerprints, etc. However, TLC identification and content determination can only qualitatively or quantitatively monitor whether a target chemical component is contained in a traditional Chinese patent medicine, and cannot to determine whether the target chemical component is derived from the corresponding Chinese herbal medicines in the prescription of the traditional Chinese patent medicine or artificially added. In addition, most of the existing methods for detecting the species in a multi-component mixture involve performing PCR-amplification on specific gene sequences followed by sequencing. In order to eliminate the limitations of the existing quality control methods for traditional Chinese patent medicines, the present invention intends to adopt the metagenomic sequencing method as supplement to the current methods.

DNA barcode molecular identification is a molecular biological technique that uses a standard and relatively short DNA sequence in the genome to identify species, and it is an effective supplement to traditional identification methods. The *Pharmacopoeia of the People's Republic of China* 2015 Edition (Volume IV) records the guiding principles for DNA barcode molecular identification of Chinese herbal medicines, and the DNA barcode molecular identification has been widely used as one of the methods for controlling the quality of Chinese herbal medicines. High-throughput sequencing technology, also known as "next-generation" sequencing technology, can perform sequencing to hundreds of thousands to millions of DNA molecules once in parallel. This technique can now be used for de novo sequencing of species without reference sequence at the genomic level to obtain the reference sequences for the species, laying the foundation for subsequent studies; whole-genome resequencing is carried out on the species with the reference sequences, mutation sites are scanned and tested to explore the molecular basis of individual differences; whole transcriptome resequencing can be used to study alternative splicing, code sequence single nucleotide polymorphism (cSNP), etc.; and small RNA sequencing can discover new microRNAs by isolating RNA molecules with specific size.

SUMMARY OF THE INVENTION

The object of the invention is to provide a method for controlling the quality of traditional Chinese patent medicines based on metagenomics, which can effectively supplement the existing quality control methods for traditional Chinese patent medicines and maintain safety of clinical medication.

The object of the present invention is achieved by the following technical solutions:

A method for controlling the quality of traditional Chinese patent medicines based on metagenomics, comprising the following steps:

1) extracting the genomic DNA of the traditional Chinese patent medicine sample to be tested;

2) constructing the library of the genomic DNA obtained in step 1) based on a high-throughput sequencing platform, and performing metagenomic sequencing;

3) filtering the raw data obtained from the metagenomic sequencing of step 2) with a sequencing data filtering software to remove the sequencing adapter and the low quality data; mapping the filtered reads to the Internal Transcribed Spacer 2 (ITS2) database (GenBank) using a short reads alignment software in order to obtain candidate short reads of Internal Transcribed Spacer 2 (ITS2) sequence from the traditional Chinese patent medicine sample to be tested, and assembling the obtained short reads by a short reads assembly software to finally obtain ITS2 sequence of the traditional Chinese patent medicine sample to be tested that can be used for subsequent analysis;

4) performing BLAST alignment on the ITS2 sequence of the traditional Chinese patent medicine sample to be tested obtained in step 3) in the DNA Barcoding System for Identifying Herbal Medicine, to obtain the species identification results;

5) comparing the obtained identification results with the labeled species of the traditional Chinese patent medicine sample to be tested to determine whether the species actually contained in the traditional Chinese patent medicine to be tested are identical to the labeled species, thereby obtaining a conclusion about the quality of the traditional Chinese patent medicine sample to be tested.

Wherein, the GenBank database is the DNA sequence database established by the National Center for Biotechnology information (NCBI).

Wherein, the DNA Barcoding System for Identifying Herbal Medicine is a system created by the present inventor's team.

Preferably, the extraction of the genomic DNA of the traditional Chinese patent medicine sample to be tested in the step 1) is carried out according to the guiding principle for DNA barcode molecular identification of Chinese herbal medicines (*Pharmacopoeia of the People's Republic of China* 2015 Edition (Volume IV)).

Preferably, the extraction of the genomic DNA of the traditional Chinese patent medicine sample to be tested in the step 1) comprises the steps of: taking 100 mg or more of traditional Chinese patent medicine samples, grinding with a FastPrep bead mill (Retsch MM400, Germany), rinsing with a pre-wash buffer until the supernatant is colorless, and extracting the genomic DNA by plant genomic DNA extraction kit.

In order to better obtain the genomic DNA of the traditional Chinese patent medicine sample, the protocol can be appropriately improved, preferably, the extraction of the genomic DNA is carried out using a plant genomic DNA extraction kit in a water bath at a temperature of 56 to 65° C. (preferably 56° C.); more preferably, the time for the extraction of the genomic DNA is 8 to 15 hours, preferably 12 hours.

Preferably, the high-throughput sequencing platform in step 2) is Illumina Hiseq 2500 or Illumina Hiseq 4000; preferably Illumina Hiseq 2500.

Preferably, the sequencing data filtering software in step 3) is TRIMMONMATIC v0.36 software.

Preferably, the short reads alignment software in step 3) is BOWTIE2 v2.2 software.

Preferably, the short reads assembly software in step 3) is VELVET v1.2 software.

Preferably, step 3) is carried out by filtering the raw data obtained from the metagenomic sequencing of step 2) with TRIMMONMATIC v0.36 software to remove the sequencing adapters and the low quality data; mapping the filtered reads to the ITS2 database (GenBank) using BOWTIE2 v2.2 software in order to obtain candidate short reads of ITS2 sequence from the traditional Chinese patent medicine sample to be tested, and assembling the obtained short reads by VELVET v1.2 software to finally obtain ITS2 sequences of the traditional Chinese patent medicine sample to be tested that can be used for subsequent analysis.

Wherein, in step 3), filtering with TRIMMONMATIC v0.36 software filter can effectively remove the sequencing adapters and low quality data to ensure the accuracy of the data for subsequent alignment and assembly.

Wherein, in step 3), mapping the filtered reads to the ITS2 database (GenBank) using BOWTIE2 v2.2 software can obtain the short reads of ITS2 sequence with high-match high-quality, and VELVET v1.2 software is used for assembling the short reads to finally obtain the ITS2 sequences that can be used for subsequent analysis.

Wherein, in step 5), if the obtained identification result is consistent with the labeled species of the traditional Chinese patent medicine sample to be tested, it indicates that the traditional Chinese patent medicine contains the ingredients of all of the species as stated;

if the obtained identification result includes the labeled species of the traditional Chinese patent medicine sample to be tested and other unlabeled species, it indicates that the traditional Chinese patent medicine contains other impurity species in addition to the labeled species; and if the obtained identification result only includes parts of the labeled species of the traditional Chinese patent medicine sample to be tested, it indicates that the traditional Chinese patent medicine is not added with the species that is stated to be contained in the traditional Chinese patent medicine but missed in the identification result, or that the DNA of the species missed in the identification result is degraded seriously.

The present invention further provides a kit for controlling the quality of traditional Chinese patent medicines based on metagenomics.

The present invention further provides the use of the method for controlling the quality of traditional Chinese patent medicines based on metagenomics in the quality monitoring of herbal products or dietary supplements.

The invention monitors the quality of traditional Chinese patent medicines based on sequencing platforms such as Illumina Hiseq 2500 and Illumina Hiseq 4000 and the like using metagenomic sequencing combined with DNA barcode molecular identification technology. The method of the present invention has wide applicability, other high-throughput sequencing platforms in addition to Illumina Hiseq 2500 are also applicable to the present invention, and the present invention can detect all samples of traditional Chinese patent medicines, herbal products, and dietary supplements whose ITS2 sequences are obtainable. Therefore, quality monitoring of traditional Chinese patent medicines, herbal products, dietary supplements and the like can be achieved.

BRIEF DESCRIPTION OF THE DRAWINGS

FIG. 1 shows the BLAST result of the Chinese herbal medicine Akebiae Caulis of Example 1.

FIG. 2 shows the BLAST result of the Chinese herbal medicine Angelicae sinensis Radix of Example 1.

FIG. 3 shows the BLAST result of the Chinese herbal medicine Gardeniae Fructus of Example 1.

FIG. 4 shows the BLAST result of the Chinese herbal medicine Glycyrrhizae Radix et Rhizoma of Example 1.

FIG. 5 shows the BLAST result of the Chinese herbal medicine Scutellariae Radix of Example 1.

FIG. 6 shows the BLAST result of the Chinese herbal medicine *Panax ginseng* as a positive control in Example 1.

FIG. 7 shows the BLAST result of the Chinese herbal medicine Aucklandiae Radix of Example 6.

SPECIFIC MODES FOR CARRYING OUT THE EMBODIMENTS

The technical solutions in the examples of the present invention will be described clearly and completely hereinafter. It is obvious that the described examples are only a part of the examples of the present invention rather than all of them. Other examples obtainable by a person skilled in the art based on the examples of the present invention without creative efforts all fall within the scope of the present invention.

Example 1

1. Materials:

The test material was the traditional Chinese patent medicine Longdan Xiegan Pill (water pill) made in the laboratory according to the prescribed dosage and preparation method in the prescription of Longdan Xiegan Pill (water pill) recorded in *Pharmacopoeia of the People's Republic of China* 2015 Edition (Volume I). In addition, in order to verify the sensitivity of the method, the Chinese herbal medicine *Panax ginseng* was added as a positive control in an amount equal to the Chinese herbal medicine having the smallest dose in the prescription.

2. Experimental Steps:

1) The prescription of traditional Chinese patent medicine Longdan Xiegan Pill consisted of ten Chinese herbal medicines including Gentianae Radix et Rhizoma, Bupleuri Radix, Scutellariae Radix, Gardeniae Fructus (stir-fried), Alismatis Rhizoma, Akebiae Caulis, Plantaginis Semen (stir-fried with salt solution), Angelicae Sinensis Radix (stir-fried with yellow rice wine), Rehmanniae Radix, and Glycyrrhizae Radix et Rhizoma (stir-fried with honey). Each of the Chinese herbal medicines used in this Example had been identified by morphology and DNA barcoding to ensure the accuracy of the species. According to the prescribed dosage and preparation method recorded in *Pharmacopoeia of the People's Republic of China* 2015 Edition (Volume I), the above-mentioned Chinese herbal medicines and the positive control *Panax ginseng* were mixed, pulverized, sieved and formulated into a pill.

2) Genomic DNA Extraction 120 mg of the above sample was ground with a FastPrep bead mill (Retsch MM400, Germany), rinsed with a pre-wash buffer until the supernatant was colorless, and extracted genomic DNA with a plant genomic DNA extraction kit (Tiangen Biochemical Technology (Beijing) Co., Ltd.) in water bath at 56° C. for 12 h. The rest steps were carried out according to the instructions for the kit.

3) Library Construction, Metagenomic Sequencing and Data Processing

In this Example, a library was constructed for the above genomic DNA based on the sequencing platform Illumina Hiseq 2500 according to the standard operating procedure of the platform, and the metagenomic sequencing was performed.

Wherein, the standard operating procedure was specifically provided as follows: genomic DNA was purified, inserted DNA fragments of 250 bp were enriched, and sequencing adapters were added to construct sequencing libraries.

The raw data obtained from the metagenomic sequencing in step 2) was filtered with TRIMMONMATIC v0.36 software, the filtered reads was mapped to the ITS2 database (GenBank) by BOWTIE2 v2.2 software to obtain effective reads of ITS2 sequence from the traditional Chinese patent medicine sample to be tested, and the selected reads was assembled by VELVET v1.2 software to obtain the ITS2 sequences.

4) Species Identification

In the DNA Barcoding System for Identifying Herbal Medicine, the ITS2 sequence of the above-mentioned traditional Chinese patent medicine sample to be tested was subjected to BLAST alignment to obtain the species identification result. After the BLAST alignment of the ITS2 sequences obtained in this Example, the following results were obtained:

Gentianae Radix et Rhizoma, Bupleuri Radix, Akebiae Caulis, Scutellariae Radix, Alismatis Rhizoma, Rehmanniae Radix, Angelicae Sinensis Radix (stir-fried with yellow rice wine), Plantaginis Semen (stir-fried with salt solution), Glycyrrhizae Radix et Rhizoma (stir-fried with honey), Gardeniae Fructus (stir-fried) and the positive control *Panax ginseng* were detected by ITS2 sequence, wherein the BLAST results of Akebiae Caulis, Angelicae Sinensis Radix, Gardeniae Fructus, Glycyrrhizae Radix et Rhizoma, Scutellariae Radix and *Panax ginseng* were shown in FIGS. 1 to 6.

The results show that the method for controlling the quality of traditional Chinese patent medicines based on metagenomics disclosed in the invention can be used for monitoring the quality of the traditional Chinese patent medicine Longdan Xiegan Pill home-made in laboratory, and has good feasibility.

Example 2

1. Materials:

The materials were basically identical to those of Example 1 except that the Chinese herbal medicine *Panax ginseng* used as a positive control in Example 1 was not added.

2. Experimental Steps:

The experimental steps were identical to those of Example 1.

After the BLAST alignment of the ITS2 sequences obtained in this Example, the following results were obtained:

Gentianae Radix et Rhizoma, Bupleuri Radix, Akebiae Caulis, Scutellariae Radix, Alismatis Rhizoma, Rehmanniae Radix, Angelicae Sinensis Radix (stir-fried with yellow rice wine), Plantaginis Semen (stir-fried with salt solution), Glycyrrhizae Radix et Rhizoma (stir-fried with honey), and Gardeniae Fructus (stir-fried) were detected by ITS2 sequence, and the test results were identical to those of Example 1 except that the Chinese herbal medicine *Panax ginseng* used as a positive control was not added.

The results show that the method for controlling the quality of traditional Chinese patent medicines based on metagenomics disclosed in the invention can be used for monitoring the quality of the traditional Chinese patent medicine Longdan Xiegan Pill made in laboratory, and has good feasibility.

Example 3

1. Materials:

The test material was a commercially available traditional Chinese patent medicine Longdan Xiegan Pill with the drug approval number (lot number: 4082410).

2. Experimental Steps:

The experimental steps were basically identical to those of Example 1 except that this Example was started from the step of DNA extraction, and then experimental operations and data processing were completed step by step until the identification of species was completed.

After the BLAST alignment of the ITS2 sequences obtained in this Example, the following results were obtained:

Gentianae Radix et Rhizoma, Bupleuri Radix, Scutellariae Radix, Angelicae Sinensis Radix (stir-fried with yellow rice wine), Plantaginis Semen (stir-fried with salt solution), Glycyrrhizae Radix et Rhizoma (stir-fried with honey), and Gardeniae Fructus (stir-fried) were detected by ITS2 sequence.

Akebiae Caulis, Alismatis Rhizoma, and Rehmanniae Radix were not detected, and the reason for this might be that the DNA of the above three species in the tested traditional Chinese patent medicine sample of this Example was degraded seriously, or that the traditional Chinese patent medicine was not added with the powders of the above three Chinese herbal medicines in the preparation process according to the provision of the *Pharmacopoeia of the People's Republic of China* 2015 Edition (Volume I).

Example 4

1. Materials:

The test material was a commercially available traditional Chinese patent medicine Longdan Xiegan Pill with the drug approval number (lot number: 4082411).

2. Experimental Steps:

The experimental steps were basically identical to those of Example 1 except that this Example was started from the step of DNA extraction, and then experimental operations and data processing were completed step by step until the identification of species was completed.

After the BLAST alignment of the ITS2 sequences obtained in this example, the following results were obtained:

Gentianae Radix et Rhizoma, Bupleuri Radix, Scutellariae Radix, wine-processed Angelicae Sinensis Radix (stir-fried with yellow rice wine), Plantaginis Semen (stir-fried with salt solution), and Glycyrrhizae Radix et Rhizoma (stir-fried with honey) were detected by ITS2 sequence.

Akebiae Caulis, Alismatis Rhizoma, Rehmanniae Radix, and Gardeniae Fructus (stir-fried) were not detected, and the reason for this might be that the DNA of the above four species in the tested traditional Chinese patent medicine sample of this Example was degraded seriously, or that the traditional Chinese patent medicine was not added with the powders of the above four Chinese herbal medicines in the preparation process according to the provision of the *Pharmacopoeia of the People's Republic of China* 2015 Edition (Volume I).

Example 5

1. Materials:

The test material was a commercially available traditional Chinese patent medicine Longdan Xiegan Pill with the drug approval number (lot number: 4082171).

2. Experimental Steps:

The experimental steps were basically identical to those of Example 1 except that this Example was started from the step of DNA extraction, and then experimental operations and data processing were completed step by step until the identification of species was completed.

After the BLAST alignment of the ITS2 sequences obtained in this example, the following results were obtained:

Gentianae Radix et Rhizoma, Akebiae Caulis, Bupleuri Radix, Angelicae Sinensis Radix (stir-fried with yellow rice wine), Plantaginis Semen (stir-fried with salt solution), and Glycyrrhizae Radix et Rhizoma (stir-fried with honey) were detected by ITS2 sequence.

Scutellariae Radix, Alismatis Rhizoma, Rehmanniae Radix, and Gardeniae Fructus (stir-fried) were not detected, and the reason for this might be that the DNA of the above four species in the tested traditional Chinese patent medicine sample of this Example was degraded seriously, or that the traditional Chinese patent medicine was not added with the powders of the above four Chinese herbal medicines in the preparation process according to the provision of the *Pharmacopoeia of the People's Republic of China* 2015 Edition (Volume I).

Example 6

1. Materials:

The test material was the traditional Chinese patent medicine YiMu Pill made in the laboratory according to the prescribed dosage and preparation method in the prescription of YiMu Pill recorded in the *Pharmacopoeia of the People's Republic of China* 2015 Edition (Volume I). In addition, in order to verify the sensitivity of the method, the Chinese herbal medicine *Panax ginseng* was added as a positive control in an amount equal to the Chinese herbal medicine having the smallest dose in the prescription.

2. Experimental Steps:

1) The prescription of traditional Chinese patent medicine YiMu Pill consisted of four Chinese herbal medicines including Leonuri Herba, Chuanxiong Rhizoma, Angelicae Sinensis Radix, and Aucklandiae Radix. Each of the Chinese herbal medicines used in this Example had been identified by morphology and DNA barcode to ensure the accuracy of the species. According to the prescribed dosage and preparation method recorded in the *Pharmacopoeia of the People's Republic of China* 2015 Edition (Volume I), the above-mentioned Chinese herbal medicines and the positive control *Panax ginseng* were mixed, pulverized, sieved and formulated into a pill.

2) Genomic DNA Extraction 120 mg of the above sample was ground with a FastPrep bead mill (Retsch MM400, Germany), rinsed with a pre-wash buffer until the supernatant was colorless, and extracted genomic DNA with a plant genomic DNA extraction kit (Tiangen Biochemical Technology (Beijing) Co., Ltd.) in water bath at 56° C. for 12 h. The rest steps were carried out according to the instructions for the kit.

3) Library Construction, Metagenomic Sequencing and Data Processing

In this Example, a library was constructed for the above genomic DNA based on the sequencing platform Illumina Hiseq 2500 according to the standard operating procedure of the platform, and the metagenomic sequencing was performed.

Wherein, the standard operating procedure was specifically provided as follows: genomic DNA was purified, inserted DNA fragments of 200 bp were enriched, and sequencing adapters were added to construct sequencing libraries.

The raw data obtained from the metagenomic sequencing in step 2) was filtered with TRIMMONMATIC v0.36 software, the filtered reads was mapped to the ITS2 database (GenBank) by BOWTIE2 v2.2 software to obtain candidate short reads of ITS2 sequence from the traditional Chinese patent medicine sample to be tested, and the selected reads were assembled by VELVET v1.2 software to obtain the ITS2 sequences.

4) Species Identification

In the DNA Barcoding System for Identifying Herbal Medicine, the ITS2 sequence of the above-mentioned traditional Chinese patent medicine sample to be tested was subjected to BLAST alignment to obtain the species identification result. After the BLAST alignment of the ITS2 sequences obtained in this Example, the following results were obtained:

Leonuri Herba, Chuanxiong Rhizoma, Angelicae Sinensis Radix, Aucklandiae Radix, and the positive control *Panax ginseng* were detected by ITS2 sequence, wherein the BLAST result of Aucklandiae Radix was shown in FIG. 7.

The results show that the method for controlling the quality of traditional Chinese patent medicines based on metagenomics disclosed in the invention can be used for monitoring the quality of the traditional Chinese patent medicine Longdan Xiegan Pill made in laboratory, and has good feasibility.

Example 7

1. Materials:

The materials were basically identical to those of Example 6 except that the Chinese herbal medicine *Panax ginseng* used as a positive control in Example 6 was not added.

2. Experimental Steps:

The experimental steps were identical to those of Example 6.

After the BLAST alignment of the ITS2 sequences obtained in this Example, the following results were obtained:

Leonuri Herba, Chuanxiong Rhizoma, Angelicae Sinensis Radix, and Aucklandiae Radix were detected by ITS2 sequence, and the test result was identical to those of Example 6 except that the Chinese herbal medicine *Panax ginseng* used as a positive control was not added.

The results show that the method for controlling the quality of traditional Chinese patent medicines based on metagenomics disclosed in the invention can be used for monitoring the quality of the traditional Chinese patent medicine Longdan Xiegan Pill made in laboratory, and has good feasibility.

Example 8

1. Materials:

The test material was a commercially available traditional Chinese patent medicine YiMu Pill with the drug approval number (lot number: 3015152).

2. Experimental Steps:

The experimental steps were basically identical to those of Example 6 except that this Example was started from the step of DNA extraction, and then experimental operations and data processing were completed step by step until the identification of species was completed.

After the BLAST alignment of the ITS2 sequences obtained in this Example, the following results were obtained:

Leonuri Herba, Chuanxiong Rhizoma, Angelicae Sinensis Radix, and Aucklandiae Radix were detected by ITS2 sequence.

The result indicates that the traditional Chinese patent medicine YiMu Pill of this Example contains all of the labeled species.

Example 9

1. Materials:

The test material was a commercially available traditional Chinese patent medicine YiMu Pill with the drug approval number (lot number: 2015395).

2. Experimental Steps:

The experimental steps were basically identical to those of Example 6 except that this Example was started from the step of DNA extraction, and then experimental operations and data processing were completed step by step until the identification of species was completed.

After the BLAST alignment of the ITS2 sequences obtained in this example, the following results were obtained:

Leonuri Herba and Angelicae Sinensis Radix were detected by ITS2 sequence.

Chuanxiong Rhizoma and Aucklandiae Radix were not detected by ITS2 sequence, and the reason for this might be that the DNA of the above two species in the tested traditional Chinese patent medicine sample of this Example was degraded seriously, or that the traditional Chinese patent medicine was not added with the powders of the above two Chinese herbal medicines in the preparation process according to the provision of the *Pharmacopoeia of the People's Republic of China* 2015 Edition (Volume I).

Example 10

1. Materials:

The test material was a commercially available traditional Chinese patent medicine YiMu Pill with the drug approval number (lot number: 2015616).

2. Experimental Steps:

The experimental steps were basically identical to those of Example 6 except that this Example was started from the step of DNA extraction, and then experimental operations and data processing were completed step by step until the identification of species was completed.

After the BLAST alignment of the ITS2 sequences obtained in this example, the following results were obtained:

Leonuri Herba and Angelicae Sinensis Radix were detected by ITS2 sequence.

Chuanxiong Rhizoma and Aucklandiae Radix were not detected by ITS2 sequence, and the reason for this might be that the DNA of the above two species in the tested traditional Chinese patent medicine sample of this Example was degraded seriously, or that the traditional Chinese patent medicine was not added with the powders of the above two Chinese herbal medicines in the preparation process according to the provision of the *Pharmacopoeia of the People's Republic of China* 2015 Edition (Volume I).

INDUSTRIAL APPLICABILITY

The present invention provides a method for controlling the quality of traditional Chinese patent medicines based on metagenomics, comprising the following steps: 1) extracting the genomic DNA of the traditional Chinese patent medicine sample to be tested; 2) constructing the library of the genomic DNA obtained in step 1) based on a high-throughput sequencing platform, and performing metagenomic sequencing; 3) filtering the raw data obtained from the metagenomic sequencing of step 2) with a sequencing data filtering software to remove the sequencing adapter and the low quality data; mapping the filtered reads to the ITS2 database (GenBank) using a short reads alignment software in order to obtain candidate short reads of ITS2 sequence from the traditional Chinese patent medicine sample to be tested, and assembling the obtained short reads by a short reads assembly software to finally obtain ITS2 sequences of the traditional Chinese patent medicine sample to be tested that can be used for subsequent analysis; 4) performing BLAST alignment on the ITS2 sequence of the traditional Chinese patent medicine sample to be tested obtained in step 3) in the DNA Barcoding System for Identifying Herbal Medicine, to obtain the species identification result; 5) comparing the obtained identification result with the labeled species of the traditional Chinese patent medicine sample to be tested to determine whether the species actually contained in the traditional Chinese patent medicine to be tested are identical to the labeled species, thereby obtaining a conclusion about the quality of the traditional Chinese patent medicine sample to be tested. The method of the present invention has wide applicability, other high-throughput sequencing platforms in addition to Illumina Hiseq 2500 are also applicable to the present invention, and the present invention can detect all samples of traditional Chinese patent medicines, herbal products, and dietary supplements whose ITS2 sequences are obtainable. Therefore, quality monitoring of traditional Chinese patent medicines, herbal products, dietary supplements and the like can be achieved. The method has high economic value and good application prospect.

What is claimed is:

1. A method for controlling a quality of traditional Chinese patent medicine based on metagenomics, comprising:
   i) extracting a genomic DNA of the traditional Chinese patent medicine to be tested;
   ii) constructing a library of the genomic DNA obtained in said i) based on a high-throughput sequencing platform, and performing metagenomic sequencing;
   iii) filtering the raw data obtained from the metagenomic sequencing of said ii) with a sequencing data filtering software to remove the sequencing adapter and the low quality data; mapping the filtered reads to the Internal Transcribed Spacer 2 (ITS2) database using a short reads alignment software in order to obtain candidate short reads of ITS2 sequence from the traditional Chinese patent medicine, and assembling the obtained short reads by a short reads assembly software to finally obtain Internal Transcribed Spacer 2 sequences of the traditional Chinese patent medicine that can be used for subsequent analysis;

iv) performing alignment on the ITS2 sequence of the traditional Chinese patent medicine obtained in said iii) in the DNA Barcoding System for Identifying Herbal Medicine, to obtain the species identification results;

v) comparing the obtained identification results with the labeled species of the traditional Chinese patent medicine to determine whether the species actually contained in the traditional Chinese patent medicine are identical to the labeled species, thereby obtaining a conclusion about the quality of the traditional Chinese patent medicine.

2. The method according to claim 1, wherein the extraction of the genomic DNA of the traditional Chinese patent medicine sample to be tested in the said i) comprises: taking 100 mg or more of traditional Chinese patent medicine samples, grinding with a bead mill, rinsing with pre-wash buffer until the supernatant is colorless, and extracting the genomic DNA by plant genomic DNA extraction kit.

3. The method according to claim 2, wherein the extraction of the genomic DNA is carried out using a plant genomic DNA extraction kit in a water bath at a temperature of 56 to 65° C.

4. The method according to claim 2, wherein the time for the extraction of the genomic DNA is 8 to 15 hours.

5. The method according to claim 1, wherein the high-throughput sequencing platform in said ii) is a high-throughput sequencing platform that has a standard operating procedure.

6. The method according to claim 1, wherein the sequencing data filtering software in said 3) is TRIMMOMATIC v0.36 software.

7. The method according to claim 1, wherein the short reads alignment software in said iii) is BOWTIE2 v2.2 software.

8. The method according to claim 1, wherein the short reads assembly software in said iii) is VELVET v1.2 software.

9. The method of claim 1, wherein the traditional Chinese patent medicines are in herbal products or dietary supplements.

10. The method according to claim 2, wherein the time for the extraction of the genomic DNA is 12 hours.

* * * * *